US011756359B2

(12) United States Patent
Caldwell et al.

(10) Patent No.: US 11,756,359 B2
(45) Date of Patent: Sep. 12, 2023

(54) HEALTH AND SANITATION MONITORING METHODS AND SYSTEMS FOR CONTROLLED ACCESS TO A PREMISES

(71) Applicant: Municipal Parking Services, Inc., Minnetonka, MN (US)

(72) Inventors: Joseph M. Caldwell, Chanhassen, MN (US); Mark J. Moran, Woodbury, MN (US); Richard W. Kelley, II, Corcoran, MN (US); Marcus N. Schmidt, Minnetonka, MN (US); David E. Collins, Jr., Colorado Springs, CO (US); James Conlan, Minneapolis, MN (US); Jason Pflaum, Wayzata, MN (US)

(73) Assignee: Municipal Parking Services, Inc., Minnetonka, MN (US)

( * ) Notice: Subject to any disclaimer, the term of this patent is extended or adjusted under 35 U.S.C. 154(b) by 199 days.

(21) Appl. No.: 17/241,752

(22) Filed: Apr. 27, 2021

(65) Prior Publication Data
US 2021/0335072 A1 Oct. 28, 2021

Related U.S. Application Data

(60) Provisional application No. 63/022,418, filed on May 8, 2020, provisional application No. 63/016,281, filed on Apr. 27, 2020.

(51) Int. Cl.
*G07C 9/25* (2020.01)
*G16H 10/20* (2018.01)
(Continued)

(52) U.S. Cl.
CPC .............. *G07C 9/25* (2020.01); *A61L 2/0088* (2013.01); *A61L 2/26* (2013.01);
(Continued)

(58) Field of Classification Search
CPC ...... G07C 9/28; G07C 9/00563; G16H 40/20; G16H 10/20; A61L 2/0088; A61L 2/26;
(Continued)

(56) References Cited

U.S. PATENT DOCUMENTS 6,882,278 B2 4/2005 Winings et al.
8,040,245 B2 10/2011 Koblasz
(Continued)

FOREIGN PATENT DOCUMENTS

WO 2008073562 A1 6/2008

OTHER PUBLICATIONS

The International Search Report and the Written Opinion rendered by the International Searching Authority for PCT/US21/29393, dated Aug. 4, 2021, 10 pages.

*Primary Examiner* — Kerri L McNally
(74) *Attorney, Agent, or Firm* — Skaar Ulbrich Macari, P.A.

(57) ABSTRACT

An automated kiosk is located adjacent to a point of access to a room or premises. The kiosk can control an automated locking mechanism for the point of access. The kiosk can read the temperature of all persons that attempt to enter the room or premises. The kiosk can also command the persons to sanitize their hands in a sanitation window of the kiosk while dispensing sanitizer and monitoring the hands of the person for effective sanitation action. The kiosk can read identification credentials, perform facial recognition, speech recognition and recognize gestures of persons. The kiosk can be further coupled to a central control computer.

20 Claims, 10 Drawing Sheets

(51) Int. Cl.

| | |
|---|---|
| *G06K 19/06* | (2006.01) |
| *G16H 40/20* | (2018.01) |
| *G08B 21/24* | (2006.01) |
| *A61L 2/00* | (2006.01) |
| *A61L 2/26* | (2006.01) |
| *G07C 9/00* | (2020.01) |

(52) U.S. Cl.
CPC .. *G06K 19/06037* (2013.01); *G06K 19/06112* (2013.01); *G07C 9/00563* (2013.01); *G08B 21/245* (2013.01); *G16H 10/20* (2018.01); *G16H 40/20* (2018.01); *A61L 2202/15* (2013.01)

(58) Field of Classification Search
CPC ....... G06K 19/06037; G06K 19/06112; G08B 21/245
USPC ...................................... 340/573.1
See application file for complete search history.

(56) References Cited

U.S. PATENT DOCUMENTS

| | | | |
|---|---|---|---|
| 8,090,155 | B2 | 1/2012 | Lacey et al. |
| 8,299,896 | B2* | 10/2012 | Mahmoodi .............. G07C 9/37 340/5.82 |
| 9,235,977 | B2 | 1/2016 | Deutsch |
| 2004/0056907 | A1 | 3/2004 | Sharma et al. |
| 2008/0136649 | A1 | 6/2008 | Van De Hey |
| 2011/0291841 | A1* | 12/2011 | Hollock ............... G08B 21/245 340/573.1 |
| 2012/0187146 | A1* | 7/2012 | Chopra ..................... A61L 2/16 222/23 |
| 2013/0033376 | A1* | 2/2013 | Seyed Momen ...... G16H 40/20 340/539.11 |
| 2013/0055588 | A1* | 3/2013 | Nakamura ............. A47K 10/48 34/565 |
| 2014/0375457 | A1* | 12/2014 | Diaz ...................... G16H 40/20 222/39 |
| 2015/0077258 | A1* | 3/2015 | Nelson ............... G06Q 30/0207 705/14.1 |
| 2016/0093081 | A1 | 3/2016 | Kim et al. |
| 2017/0215655 | A1 | 8/2017 | Ophardt et al. |
| 2019/0139395 | A1* | 5/2019 | Rogachev ............ A47K 5/1217 |

* cited by examiner

HEALTH AND SANITATION MONITORING METHODS AND SYSTEMS FOR CONTROLLED ACCESS TO A PREMISES

PRIORITY

This Application claims priority to and the benefit of U.S. Provisional Patent Application No. 63/016,281, filed Apr. 27, 2020, and U.S. Provisional Patent Application No. 63/022,418, filed May 8, 2020, both of which are incorporated fully herein by reference.

FIELD

The present invention relates generally to access control systems and, more particularly, to integrated health monitoring and access control systems to ensure that persons entering a room or premises satisfy certain sanitation actions and meet certain health criteria.

BACKGROUND

In order to reduce the spread of communicable diseases it is helpful to ensure that all persons entering a controlled space, such as a place of business, meet certain health criteria and perform certain sanitation actions. It is costly to task an employee with monitoring inbound persons to the place of business with performing this monitoring, and that employee would be at greater risk of infection as a result of performing the monitoring task. Therefore, there is a need to provide automated systems and methods for performing the health and sanitation monitoring of persons attempting to enter a premises or room through a point of access.

SUMMARY

The present invention provides unique devices, systems and methods for managing access control, sanitation monitoring and health monitoring. An automated kiosk is located adjacent to a point of access to a room or premises. The kiosk can control an automated locking mechanism for the point of access. The kiosk can read the temperature of all persons that attempt to enter the room or premises. The kiosk can also command the persons to sanitize their hands in a sanitation window of the kiosk while dispensing sanitizer and monitoring the hands of the person for effective sanitation action. The kiosk can read identification credentials, perform facial recognition, speech recognition and recognize gestures of persons. The kiosk can be further coupled to a central control computer.

The disclosure includes a kiosk, a system for managing access to a premises and a method of evaluating a person attempting to gain entry to a premises by an automated kiosk.

The kiosk can include a housing with various components provided thereto. The housing can comprise a hollow interior and a central opening defined horizontally through the housing. A display screen can be provided to the housing that faces horizontally outward from the housing. A thermal imaging sensor can be provided to the housing and located such that the thermal imaging sensor can read a body temperature of a person standing adjacent to the kiosk. A user-facing camera can be provided to the housing and located such that the user-facing camera can capture an image of the person standing adjacent to the kiosk. A dispenser nozzle can be provided to the housing and located such that a metered quantity of hand sanitizer can be dispensed on a hand of the person standing adjacent to the kiosk when the hand is placed in the central opening.

The kiosk can further comprise an optical sensor provided to the housing and located such that the optical sensor can monitor the hand of the person standing adjacent to the kiosk when the hand is placed in the central opening. A speaker and a microphone can be provided to the housing. An access card reader can be provided to the housing. An access door can be defined in the housing and located such that at least some internal components of the kiosk can be accessed when the door is opened. A sanitizer reservoir and pump can be provided inside of the housing. The pump can be fluidically coupled to the sanitizer reservoir and to the dispenser nozzle.

A light can be provided to the central opening and located such that the light illuminates the hand of the person standing adjacent to the kiosk when the hand is placed in the central opening. The light provided to the central opening can be configured to change colors to signify that the person standing adjacent to the kiosk has successfully sanitized their hand.

A processor, memory and wireless transceiver can be disposed within the housing. The processor can be coupled to the memory, the wireless transceiver, the display screen, the user-facing camera and the thermal imaging sensor. The processor can be configured to execute software code stored in the memory to perform an evaluation of the person standing adjacent to the kiosk.

The evaluation of the person standing adjacent to the kiosk can comprise reading an identification of the person standing adjacent to the kiosk. Reading the identification of the person standing adjacent to the kiosk can comprise facial recognition. The evaluation of the person standing adjacent to the kiosk can comprise reading the body temperature of the person standing adjacent to the kiosk with the thermal imaging sensor. The evaluation of the person standing adjacent to the kiosk can comprise issuing a health query to the person standing adjacent to the kiosk and utilizing gesture recognition to recognize a response to the health query by the person standing adjacent to the kiosk. The evaluation of the person standing adjacent to the kiosk can comprise issuing a health query to the person standing adjacent to the kiosk and utilizing voice recognition to recognize a response to the health query by the person standing adjacent to the kiosk.

The kiosk can be networked with a central control computer. The processor can be configured to transmit a result data from the evaluation of the person standing adjacent to the kiosk. The processor of the kiosk can be configured to issue the person standing adjacent to the kiosk a quick-response (QR) code upon completion of the evaluation. The processor of the kiosk can be configured to unlock a door upon completion of the evaluation.

The method of evaluating a person attempting to gain entry to a premises by an automated kiosk can include the automated kiosk: recognizing the presence of a person standing adjacent to the kiosk, reading a body temperature of the person standing adjacent to the kiosk, determining an identity of the person standing adjacent to the kiosk, dispensing a quantity of hand sanitizer upon a hand of the person standing adjacent to the kiosk, monitoring the hand of the person standing adjacent to the kiosk to ensure that proper sanitization of the hand is performed, issuing a series of health queries to the person standing adjacent to the kiosk, and recognizing a response to the health queries by the person standing adjacent to the kiosk. The kiosk can unlock a point of access of the premises to permit entry to the premises. The kiosk can maintain a tally of persons allowed entry to the premises.

The kiosk disclosed herein can be coupled to a point of access control system to form an integrated health monitoring and access control system.

The above summary is not intended to limit the scope of the invention, or to describe each embodiment, aspect, implementation, feature or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
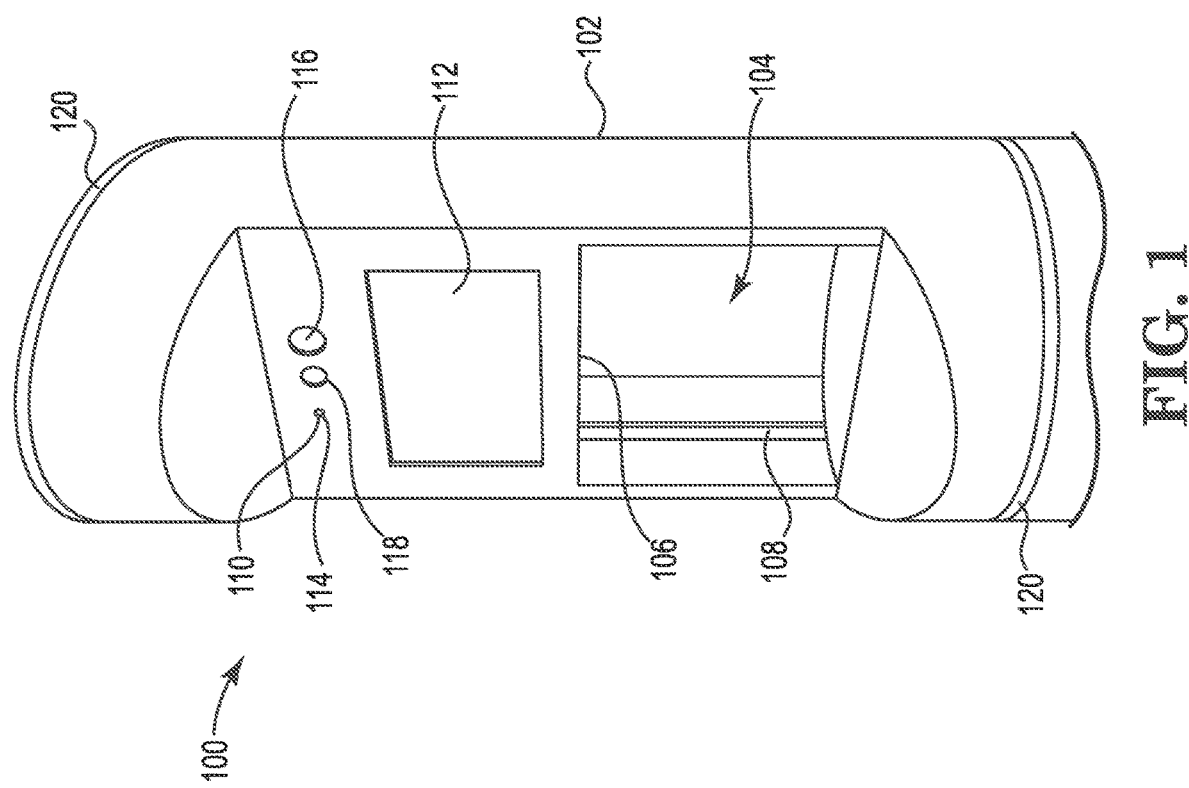
FIG. 1 is a perspective view of an upper portion of a kiosk for an integrated health monitoring and access control system according to certain example embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Referring to FIGS. 1-11, a kiosk 100 for a health evaluation and access control system is illustrated. The kiosk 100 is a non-contact device that automatically reports body temperature, manages access control and creates a comprehensive audit trail regarding persons that attempt to access a room or premises via an access control point coupled to the kiosk.

Figure 4:
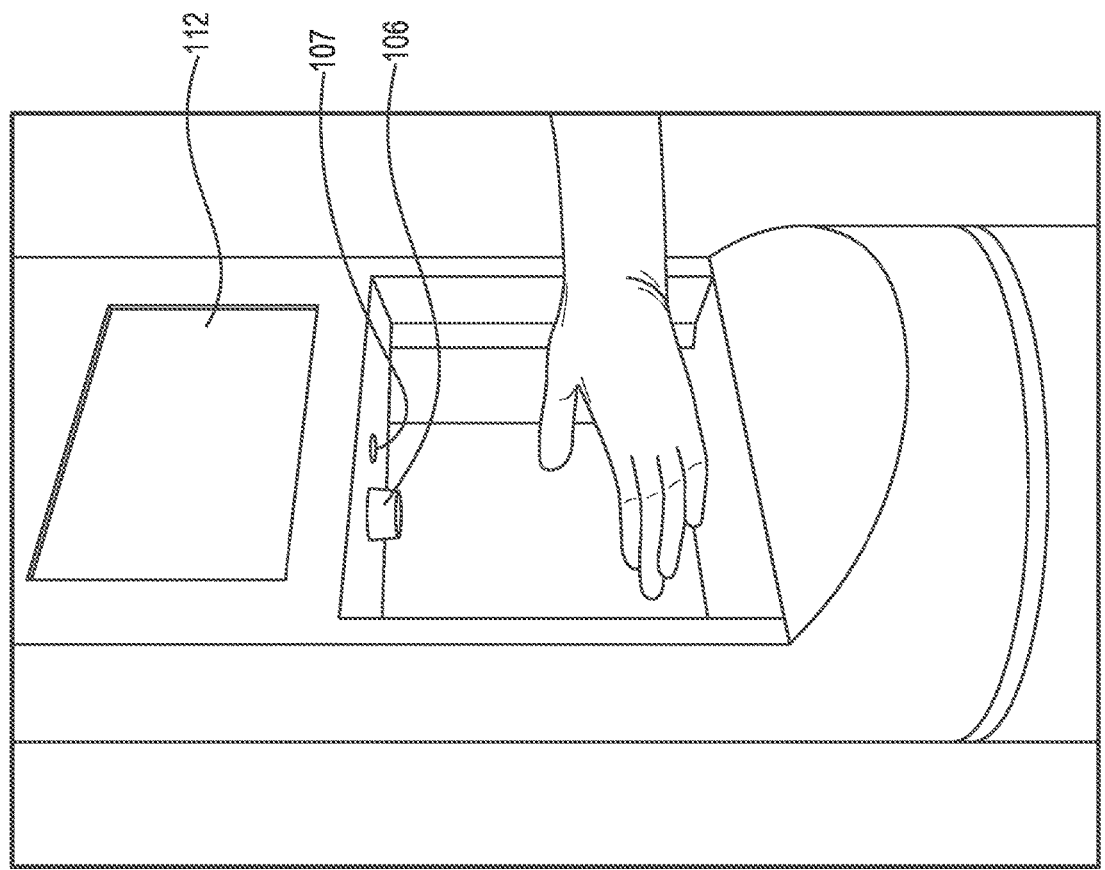
FIG. 4 is a perspective view of a portion of a kiosk for an integrated health monitoring and access control system according to certain example embodiments.

Referring more specifically to FIGS. 1 and 4-11, the kiosk 100 comprises an elongated body or housing 102 defining a central opening 104. The central opening 104 is sized to allow the user to place their hands below an automated dispensing nozzle 106 to receive a defined quantity of hand sanitizing solution as illustrated in FIG. 4. A sanitizing solution reservoir (e.g. two gallons) is disposed inside of the body 102 and coupled to the dispensing nozzle 106, which is controlled by the processor inside of the kiosk.

An optical sensor 107, such as a camera, can be located inside of the housing 102 and positioned such that the optical sensor 107 views the area of the central opening adjacent to the dispensing nozzle 106. For example, the optical sensor 107 (e.g. camera) is positioned such that it views downward from the top section of the housing perimeter forming the central opening 104. This positioning allows the optical sensor 107 to look down upon the hand or hands of the user to ensure that the user's hands are placed to receive the sanitizing solution from the nozzle 106 and that the user successfully sanitizes their hands with the sanitizing solution. The dwell time of the user's hands within the central opening 104 and the particular hand motion employed by the user can be monitored via the optical sensor 107 to ensure that the sanitizing of the user's hands is successfully completed.

Lights 108 can be provided to the perimeter of the central opening 104 to illuminate the user's hands during sanitation. This aids the optical sensor 107 operation and gives the user an indication of where to place their hands, and for how long. The lights 108 can change color to provide the user with an indication of a successful sanitization. For example, the lights can change from white to green upon successful completion of sanitization. Similarly, the lights can be changed from white to red if the user fails to receive the sanitizer on their hands and/or fails to perform the sanitization of their hands in a satisfactory manner (e.g. inadequate dwell time and/or motion).

The user can be provided with verbal instructions via a built-in speaker 110 to the kiosk, as well as receive visual information and instructions on a display screen 112 provided to the body 102 and which faces the user. The display screen 112 can also be provided with touch-sensitivity functionality to allow the user to interact with the screen.

A microphone 114 is provided to the body 102 to allow for capture of the user's voice. The processor is disposed in the housing 102 and programmed to control the various kiosk functions. The processor can also process the user's verbal commands sensed by the microphone 114 via language recognition software so that the user never needs to contact the kiosk.

The body 102 of the kiosk 100 also includes a touchless infrared thermometer or thermal imaging sensor 116. This sensor allows the kiosk 100 to read the body temperature of the user from a short distance (e.g. 2-3 feet) away from the thermal imaging sensor 116 in a relatively quick time (e.g. 1 second). The accuracy is preferably within an error range of 0.2 degrees.

The body 102 of the kiosk 100 further includes a user-facing camera 118 to capture a picture of the user that the kiosk 100 is evaluating. The user-facing camera 118 can be a high-definition camera so that the resolution can be sufficiently high to permit facial recognition (or other biometric reading, such as a retinal scan for example) based upon the image data. Image data from the user-facing camera 118 can be stored in onboard memory and/or transmitted to a remote computer or storage system (e.g. central control computer 204). The facial recognition can be performed by the processor in the kiosk 100 or by a remote computing system (e.g. the central control computer 204).

One or more LED indicator lights 120 can be provided to the body 102 to indicate operating status, evaluation status and also provide cosmetic enhancement. The color of the LED indicator lights 120 can be altered by the processor in the kiosk 100 to give an indication of status (e.g., blue is standby state, green is for permitted user entry, yellow during user evaluation and red if user entry is denied). The LED indicator lights 120 can also be solid or flashed to designate further indicator states. The LED indicator lights 120 can coordinate with a verbal indication to the user of status or state of the kiosk.

Referring particularly to FIGS. 1 and 6-11, the housing 102 of the kiosk 100 is vertically elongated so that the various components that interact with the user are located at a convenient location as will be described further below. The housing 102 itself is hollow so that the electronics can be protected and so that the kiosk 100 presents a clean and attractive appearance. Generally, the kiosk housing 102 comprises an upper portion 122 disposed atop a lower portion 124. The lower portion is then disposed atop a base plate 126. The base plate has a larger diameter than the upper or lower portions to resist tipping forces when the kiosk is installed in a free-standing position. The base plate 126 can also be anchored to the floor for added security.

Figure 5:
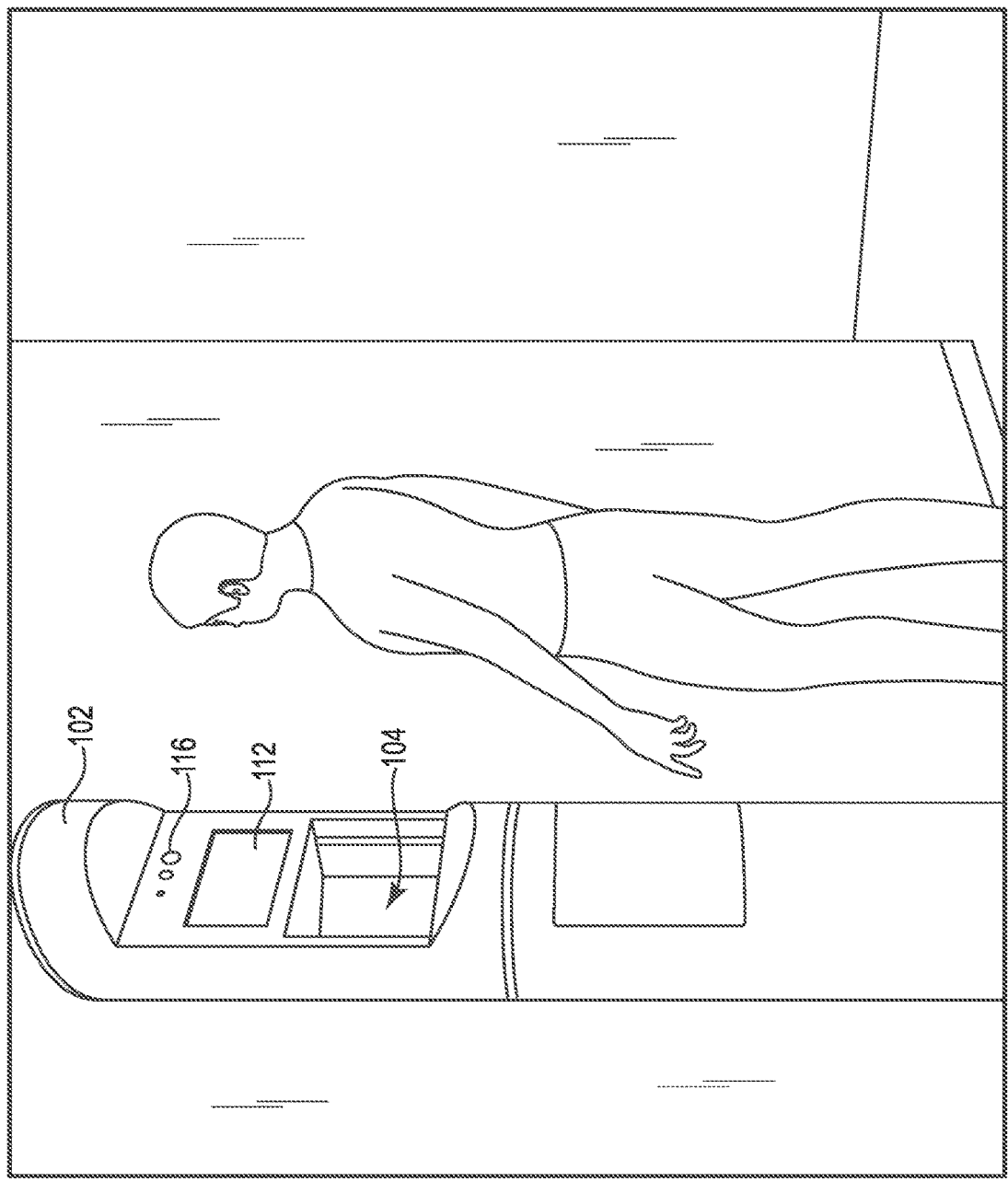
FIG. 5 is a perspective view of a kiosk for an integrated health monitoring and access control systems according to certain example embodiments.
Figure 6:
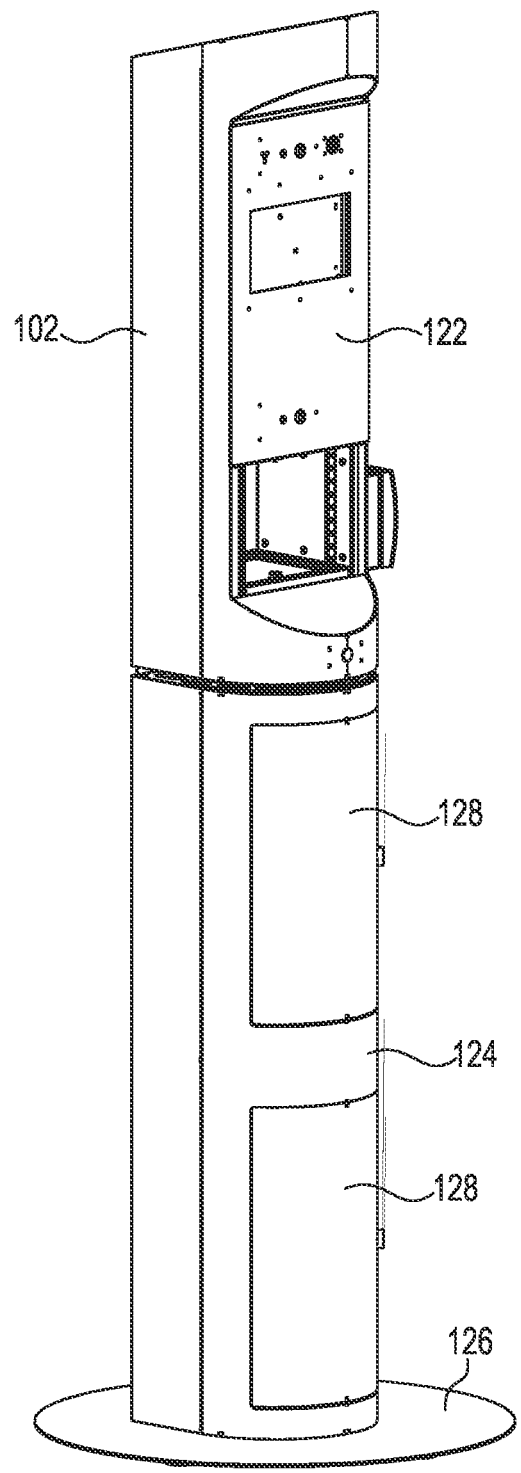
FIG. 6 is a perspective view of a kiosk according to certain example embodiments.
Figure 7:
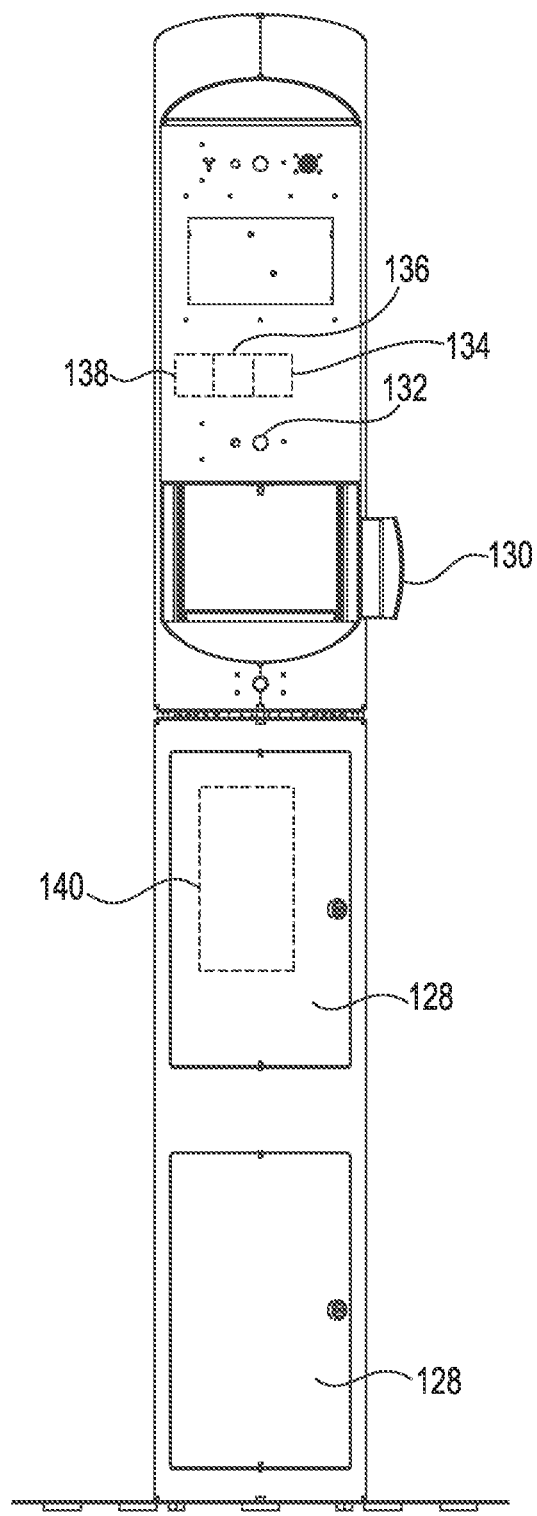
FIG. 7 is a front view of a kiosk according to certain example embodiments.
Figure 8:
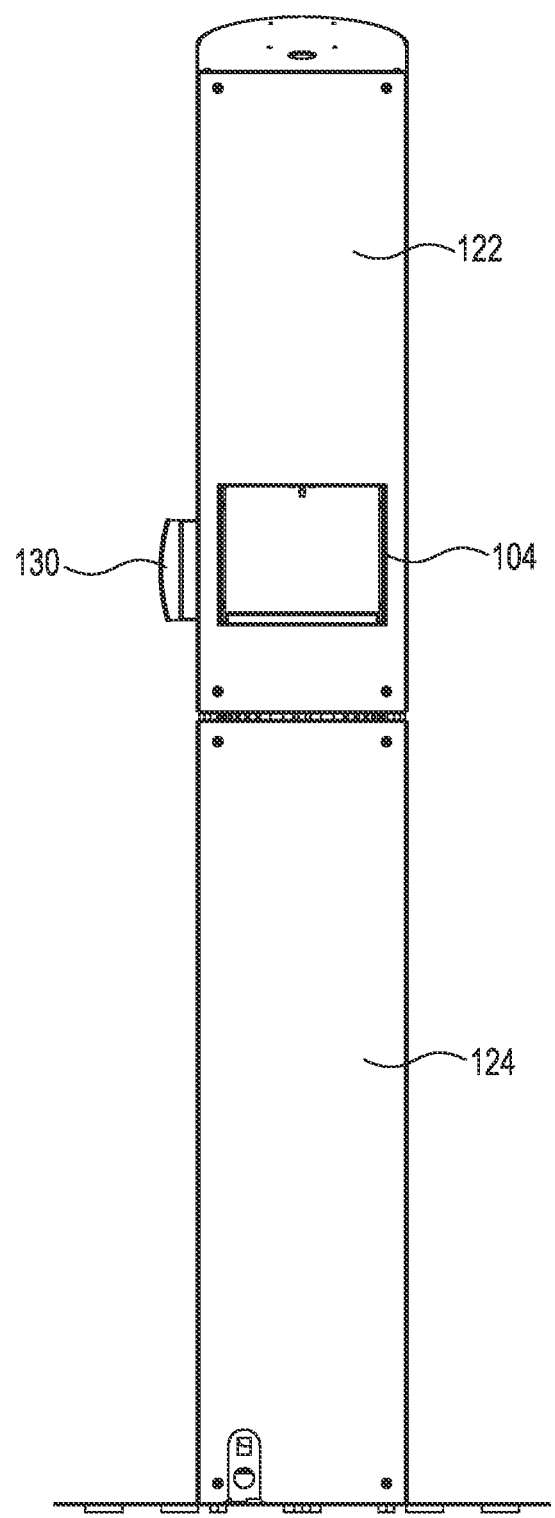
FIG. 8 is a perspective view of a kiosk according to certain example embodiments.
Figure 9:
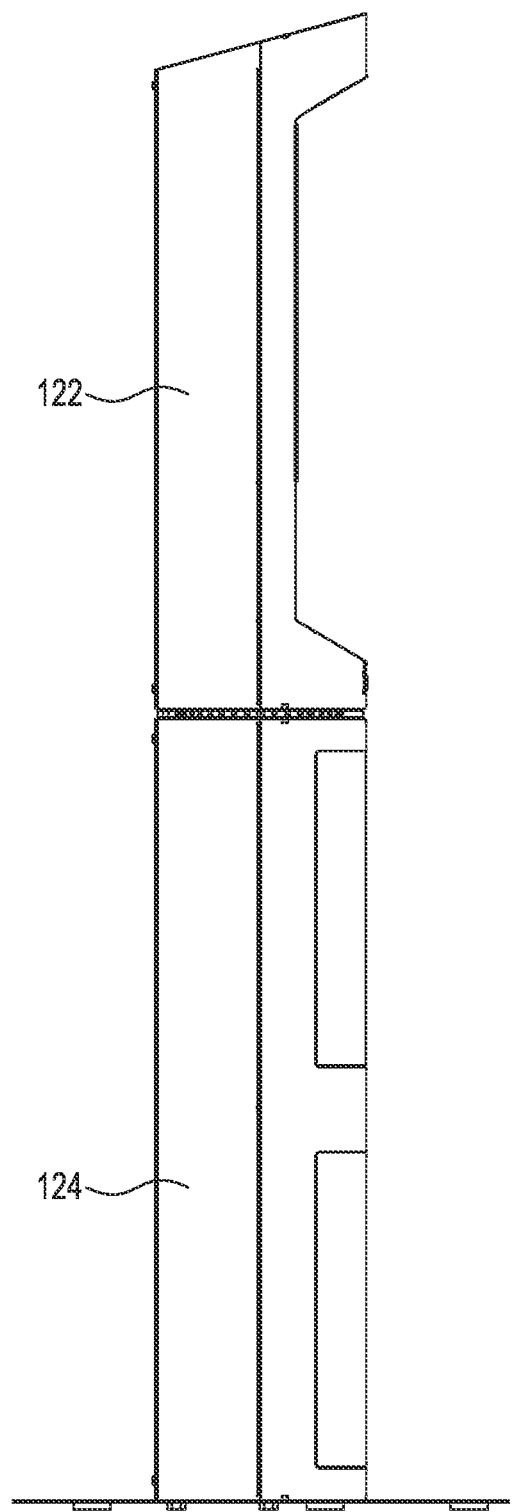
FIG. 9 is a side view of a kiosk according to certain example embodiments.
Figure 10:
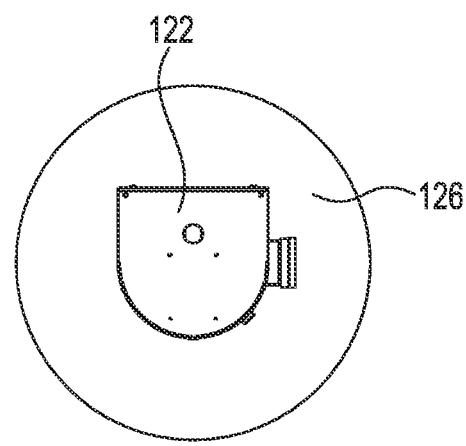
FIG. 10 is a top view of a kiosk according to certain example embodiments.
Figure 11:
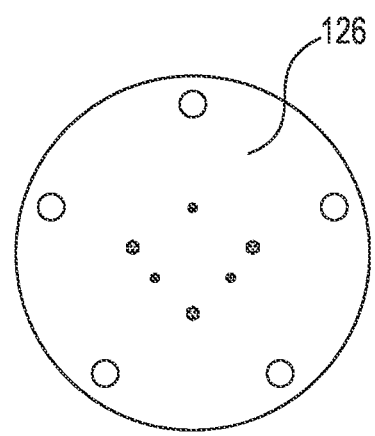
FIG. 11 is a bottom view of a kiosk according to certain example embodiments.

The housing 102 can define a flat or planar back side so that the kiosk can be installed against a vertical wall such as is shown in FIG. 5. In such installation, the base plate 126 is not used.

The lower portion 124 comprises one or more access doors 128. The doors can be secured with locks. The doors 128 provide maintenance access to internal electronic components such as the processor, memory, sanitizer reservoir, sanitizer pump etc.

The upper portion defines the central opening 104 at a convenient height between approximately the waist and shoulders of an average human adult. The central opening 104 can also be formed as a recess instead of a complete pass through opening in the housing 102. The display screen 112 is located vertically above the central opening 104 so that it is approximately at eye level with an average adult human. The thermal imaging sensor 116 and user-facing camera 118 are both located above the display screen 112 for ease of imaging and sensing of the face of the user. The speaker and microphone port 110, 114 is also disposed atop the display screen 112. The LED indicator lights 120 are provided both at the top edge and below the central opening. Of course, alternate locations for the above-noted components can be provided on alternate embodiments. For example, the speakers 110 can be to the sides of the display screen and the microphone 114 can be located anywhere adjacent to the display screen. Other alternative locations for components can also be provided in further embodiments.

FIGS. 6-9 and 10 show an access card reader 130 disposed on a side of the housing 102. Any type of card reader can be coupled to the kiosk (and the processor therein) to allow for the reading of access cards and other types of access credentials that may be issued to restrict access to a space.

A motion sensor or a proximity sensor 132 can be provided to the kiosk to sense the presence of a user that needs to undergo evaluation. Alternatively, the user-facing camera 118 can be used to determine the presence of a person in proximity to the kiosk 100 that needs to be evaluated by the kiosk 100. For example, machine imaging techniques such as background subtraction and/or edge detection can be used on image or video data to determine the user's presence. Radar or magnetic sensors can be used as alternatives to image sensors and cameras.

As described above, and as indicated in FIG. 7, the kiosk 100 further includes a processor 134 and associated memory 136 disposed inside of the housing 102. A wireless transceiver 138 can be disposed inside of the housing and coupled to the processor so that the kiosk can communicate wirelessly with other devices or to a remote computing system (e.g. via Wi-Fi, Cellular, Bluetooth, NFC, RFID or other wireless protocols) such as the central control computer 204. The processor 134, memory 136 and/or wireless transceiver 138 can each be integrated on a single circuit board, can be maintained on separate circuit boards, or can be integrated in a single chip, or any combination thereof. Connectivity with other devices and computing systems can also be provided via physical wire conduit (e.g. CAT5/6 Ethernet with RJ45 connectors).

The memory 136 may include one or more non-volatile storage devices and/or one or more volatile storage devices (e.g., random access memory (RAM)). Computer readable program code is stored in the memory. The computer readable program code is configured such that when executed by a processor, the code causes the kiosk and its components to perform the steps of the invention described herein.

The health evaluation parameters for the user can be programmed or set as desired. For example, the acceptable user temperature threshold parameter can be programmed as desired. This parameter and other operating parameters can be set remotely via the central control computer 204, or via other computer terminal communicating with the kiosk 100 directly or indirectly. Any of the evaluation steps for the overall evaluation process can also be added or subtracted. For example, the step of evaluating the person's body temperature can be omitted in certain embodiments.

The kiosk 100 can be programmed to employ facial recognition (or other biometric parameter) via the user-facing camera 118 to allow entry into a controlled space for persons that have been recognized as authorized entry and whom have satisfied the health evaluation parameters set by the administration. The kiosk 100 can document temperature readings associated with the user's faces and identifications, store such data in memory and/or transmit such data to a remote computer or database.

The user-facing camera 118 can also be employed to evaluate whether the individual desiring entry to the controlled space is wearing a mask, and correctly wearing that mask. Using machine vision analysis from the video feed from the user-facing camera 118, the kiosk's processor 134 (or a central control computer networked with the kiosk) can analyze the video and determine whether the person being imaged is wearing a mask. For example, it can be recognized that the user's mouth and/or nose can (or cannot) be seen. If the user's mouth and/or nose can be seen, then it can be determined that no mask is being worn. Alternatively, if the user's mouth and/or nose cannot be seen, then it can be determined that the user is wearing a mask. The camera can also look for the presence of an identifying mark on a mask, such as a bar code or QR code. Whether the user is wearing a mask can be logged and also be used as a pre-condition for being granted access to the controlled space.

The user-facing camera 118 can further be used to evaluate the type of mask that the user is wearing. This can be implemented, for example, by looking for a particular shape of the mask. It can also be implemented by looking for identifying markings on the mask, such as for example, QR codes, bar codes and other identifying marks.

The user-facing camera 118 can also be configured to read QR codes and other machine-readable tags. For example, the user can hold a smartphone display of a QR code towards the user-facing camera 118 and the camera will read the code. Alternatively, another camera or optical reader can be provided to the kiosk 100 for reading QR codes and the like.

The kiosk 100 can be integrated with various access control systems employed at controlled points of entry, including doors, gates and turn-styles. In further embodiments, the point of access does not have a physical barrier, such as a door, but instead, lights and/or alarms can be employed to bring attention to the appropriate personnel that a person being evaluated has been denied passage/entry. A further and more urgent indication can be provided if the person denied access attempts to access the controlled space despite such denial.

The display screen 112 can provide the user with live video communication on demand with human resources personnel, security personnel and/or health care professionals. The display screen 112 can also be used to display public service announcements, news feeds, weather notices, advertisements and other information.

The processor 134 can maintain a tally of the occupancy of the controlled access space. Entry of a person can be denied when the occupancy tally reaches a preset threshold maximum number. The total number of persons that have accessed the particular controlled access space by the kiosk can also be tracked with any desired frequency (e.g. daily) and the specific identities of all persons permitted entry (and denied entry and reasons therefore) can be logged and reported as desired. Persons exiting the controlled space can also be monitored with a camera coupled to the kiosk 100 (or the central control computer 204) to reduce the tally of occupants, so that a total number of occupants within a particular controlled space is always known to the processor 134 of the kiosk 100.

The kiosk can output any data that it collects and send such collected data to a third party computer system, such as a biometric system, via application programming interfaces (APIs).

The kiosk 100 can be programmed to interact with users in any desired language. The user can request a language change, if desired, or the kiosk 100 can be programmed to recognize the particular language being spoken by the user and automatically change the language of the prompts to match the language of the user.

Figure 2:
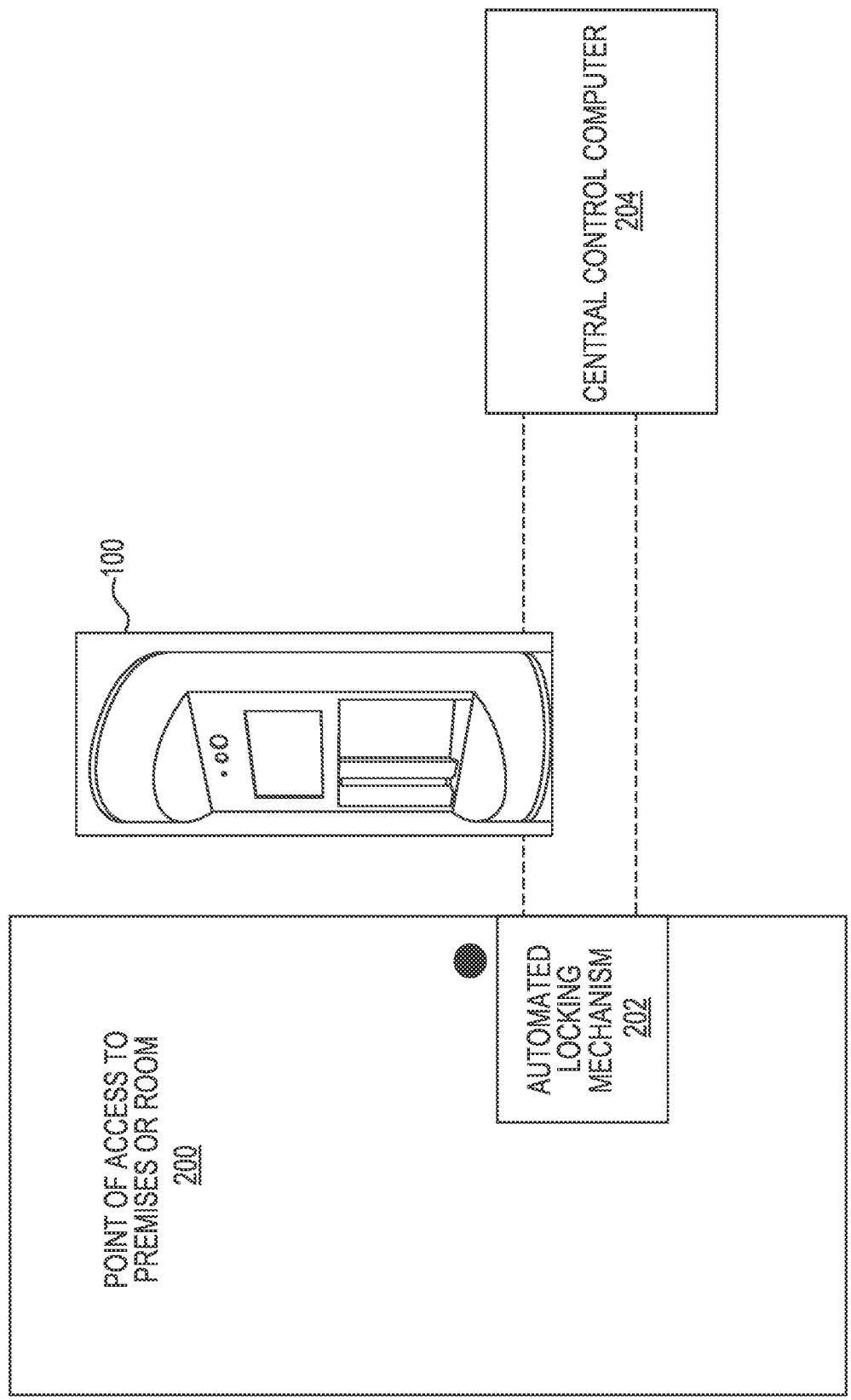
FIG. 2 is a diagram of an integrated health monitoring and access control system according to certain example embodiments.

Referring to FIG. 2, in use, a user approaches a point of access to a premises or room 200. In this example, the point of access 200 is a door. However, the point of access can be any access control device, such as a gate, a turnstile, etc. The door is maintained in a default locked condition by an automated locking mechanism 202. The kiosk 100 is coupled to the automated locking mechanism 202 so that it can actuate the automated locking mechanism 202 to unlock the door only if the user is permitted entry by the kiosk following an evaluation. The kiosk 100 is also coupled to a remotely-located central control computer 204.

Upon approaching the kiosk 100 located adjacent to the door, the identification of the user is evaluated to determine if the user is authorized to access the room 200. As discussed above, this part of the evaluation may involve a facial recognition or other biometric determination. Alternatively, the user can present a key-card, QR code, or other credential that is read by the kiosk 100. The tally of occupants is also checked to determine whether the user can enter the room 200 without exceeding occupancy limits.

If the room 200 is not subject to access by only limited specific individuals (e.g. the room is a public space such as a restaurant), the kiosk can request that each user present an identification for contact tracing purposes. For example, a government issued identification (e.g. driver's license, passport, etc.) can be scanned and stored in memory by the kiosk 100, and such data can be transmitted to the central control computer 204 as well. Persons refusing to present identification can be denied entry to the room 200.

If the user is authorized for access to the room 200 according to the steps above, then the kiosk 100 proceeds to the health evaluation and sanitization evaluation steps. The user can be evaluated for their body temperature by the thermal imaging sensor 116. If the user's temperature is measured to be below the preset threshold, then the user is instructed to sanitize their hands. If the user's temperature is measured to be above the preset threshold, then the user is indicated/told that their access is denied.

The user can further be queried with a series of health questions to which the user must provide an affirmative or negative feedback to the kiosk. The feedback can be in verbal form, or the user-facing camera can determine whether the user nods affirmatively or shakes their head negatively, or the user can physically touch the display screen 112, or any combination of inputs can be employed. Other gestures of the user can also be recognized, such as hand motion gestures. Use of non-touch gestures avoids the need for a user to contact the kiosk 100.

For example, the person can be queried whether they have had a fever above 100 degrees in a preceding time period (e.g. past two weeks), whether they have traveled outside of the country in the preceding time period, whether they have been exposed to a person that has been diagnosed with a particular condition in a specified preceding time period, whether they have a sore throat or a cough, or have any other indication of a disease that the administrator may deem relevant to entry to the room 200. If the person being evaluated answers affirmatively to any of the queries, then the person may be denied entry and/or connected to medical, human resources, or security personnel to determine whether to allow access to the controlled space.

The person being evaluated can also be queried whether they have been immunized for a specific disease or pathogen. Proof of immunization (e.g. an immunization card) can be scanned or recognized and such data stored in memory. The kiosk 100 can be programmed to only permit entry to the room 200 to persons that have been immunized against specific viruses and other pathogens.

If access is denied based upon temperature or other symptom of disease, then the user can be instructed by the display screen to report to a medical facility for evaluation as to the cause of their elevated temperature and/or be evaluated for presence of a disease. The user may also be connected to medical personnel via the display screen to have any questions answered and/or receive further instructions. The medical personnel can be enabled with the opportunity to override the kiosk's temperature denial based upon the discretion of the medical personnel.

If the user passes a medical test for the presence of a disease of concern to the administration, then the user can be given a QR code by the testing personnel that is valid for a limited time that will allow them to bypass the health screening questions for as long as the QR code is valid.

In a further embodiment, once a user is evaluated for health by a kiosk on a particular day, that user can be given a health pass QR code, either physically (e.g. a paper printout) or electronically (e.g. sent to the user's smartphone) to allow the user to bypass health screenings by that same one or other designated kiosks that same day, days or part of a day.

The QR code mentioned herein is understood to represent any type of machine-readable optical label that contains information.

Once the user passes the temperature scan, they are instructed to insert their hands into the central opening 104 of the kiosk 100 to perform a sanitizing procedure. The optical sensor 107 in the central opening 104 senses that the user's hands are present and dispenses the defined quantity of sanitizing solution. A reservoir and pump 140 are provided inside of the housing to store and controllably dispense the sanitizer. The pump is coupled to the processor to enable the control of the dispensing.

Upon dispensing of the sanitizer, the user is verbally instructed, textually instructed on the display screen and/or visually explained with depictions via the display, to spread the sanitizer over their hands completely and to employ a certain hand motion for a pre-set period of time. The optical sensor 107 confirms that the hand sanitizing duration and motion is acceptable according to preset parameters programmed into the processor.

If the hand sanitizing task is successfully completed by the user being evaluated, then the kiosk 100 indicates a successful result to the user. The indication can be verbal, via text on the display screen 112 and/or by changing the color of the lights 108 and/or 120. The kiosk 100 unlocks the locking mechanism of the door to the room 200 to allow the user to enter the controlled access room 200 or premises. If the hand sanitizing procedure is not attempted, or if it is not fully completed correctly, then the user is advised of their failed result (e.g. via the same means as the positive result noted above). The user can be instructed to repeat the sanitation process and their attempt will be reevaluated. A repeated failure can be reported to security personnel, human resources personnel and/or medical personnel by the kiosk 100.

In an additional evaluation, the sanitizer can include a specific recognizable scent (e.g. orange citrus). The kiosk 100 can prompt the user being evaluated to identify the particular scent in order to test whether the user's sense of smell is functional. Alternatively, the kiosk 100 can be configured to emit a particular scent from a scent reservoir (disposed within the housing) as the basis for the sense of smell evaluation.

The person can also be evaluated to determine that they are wearing a mask properly prior to authorizing entry.

The evaluation procedures of the kiosk can comprise some or all of the procedures explained above. Additional evaluation procedures not mentioned above can also be performed. The particular procedures performed can also vary depending on a classification of the person being evaluated. For example, a person being evaluated may be classified as a medical personnel or security personnel and will then be exempt from one or more of the evaluation steps. Also, persons that have been evaluated earlier in the same day can be exempted from one or more of the evaluation steps.

The determinations of classification of being a previously-evaluated persons can be performed by matching the person's identification during the identification step against a classification database maintained by the central control computer 204. The matching step can be performed by the kiosk 100 sending the identification data to the central control computer 204 for the determination, or the kiosk 100 can query the database directly.

The administrator can enable and disable certain steps of the evaluation procedures to be performed on personnel by the kiosk as desired.

Images of all persons evaluated by the kiosk 100 are captured and logged along with all data collected or evaluated, which can include a time stamp, identification data, classification, health query results, temperature result, mask result, and hand sanitizing result. The hand sanitizing process sensor data can also be stored. Biometric identification data can also be stored if employed. Occupancy tally data can also be logged. All of this data can be stored onboard the kiosk 100 in memory 136. The data can also be transmitted to the central control computer 204 for report generation, coordination between kiosks, and future reference.

The present kiosk uses any one or more evaluation criteria discussed herein to determine whether the person being evaluated can be granted access to the controlled space: successful completion of hand sanitizing, wearing a mask and/or body temperature below a pre-set threshold. For example, the kiosks can be configured to evaluate only the dispensing of hand sanitizer upon the user's hands.

The kiosk 100 can be programmed to determine which, if any, of the evaluation results will be deemed to be a failed result such that entry is denied to the controlled space 200. In an alternative embodiment, the user is not denied entry, but their results are stored in memory for later recall if an evaluation becomes necessary.

Figure 3:
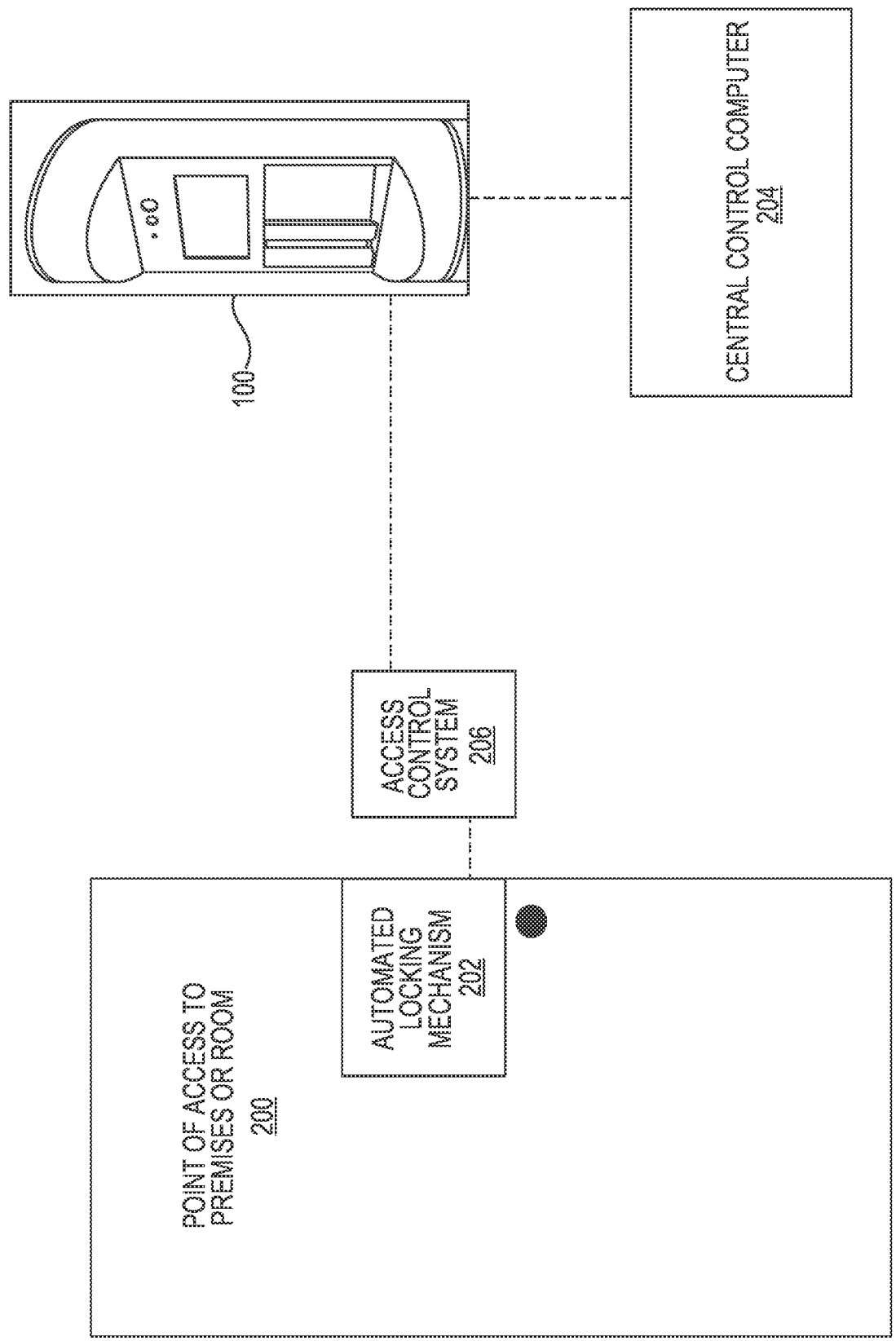
FIG. 3 is a diagram of an integrated health monitoring and access control system according to certain example embodiments.

Referring to FIG. 3, an alternative configuration is shown where the kiosk 100 interfaces with an already existing access control system 206, such as for example, a keycard access system. The existing access control system 206 operates the automated locking system 202 of the point of access to the controlled space 200. The kiosk 100 does not directly operate the automated locking mechanism 202. Instead, the kiosk 100 performs its evaluation(s) of the person as explained herein and then indicates to the access control system 206 that the person may gain access if the person possesses the proper access rights according to the access control system's normal evaluation. This arrangement allows for the kiosk 100 to be easily retrofit to existing access control systems.

One example way that the kiosk 100 can provide an indication to the access control system 206 that the person may gain access if the person possesses the proper access rights according to the access control system's normal evaluation is to provide the kiosk 100 with control over the power supply for the access control system 206. In this example, the access control system 206 is normally maintained in a de-powered state by the kiosk 100. Only when the kiosk 100 determines that the person being evaluated has passed the evaluation(s) does the kiosk 100 enable power to the access control system 206 so that the person can interact with the access control system 206 in the usual manner. Then after the person passes through the point of access 206 (or upon the lapse of a timer), the access control system 206 is de-powered again. A magnetic sensor provided to the point of access, or feedback from the access control system 206, can be used by the kiosk 100 to determine that the point of access has opened and closed again. Of course, other means for locking out the operation of the access control system 206 by the kiosk 100 can be employed as well.

In a further embodiment, the kiosk 100 can function as an evaluation system prior to issuing a ticket to the user for public transportation, such as for a subway, bus, train, boat, etc., or into a location of mass gathering where a ticket is required, such as a concert, sporting event, etc. In such employments, the kiosk 100 can scan the ticket or match the persons with a list of ticket holders as part of the evaluation prior to granting access.

The kiosk 100 can be employed to evaluate a person entering a premises, or it can be employed to evaluate access to particular spaces within the premises. For example, the kiosk 100 can be employed to ensure that persons entering a break room within the business premises have satisfactorily applied sanitizer to their hands.

The kiosk 100 can further be configured to wirelessly communicate with contact tracing software on a user's smartphone via APIs. The processor in the kiosk 100 can use the contact tracing data to determine whether the user is too high of a risk to be authorized entry to the controlled space. Conversely, the kiosk 100 can push contact tracing data to the user's smartphone to enhance the effectiveness of the contact tracing software.

In a further embodiment, a smartphone app can be provided to the user's smartphone to enable the user to interact with the kiosk 100 via the smartphone app. The user can enter their identification information via their smartphone and answer the health query questions via smartphone for example. The kiosk 100 can also sense the presence of the user via the presence of their smartphone since the Bluetooth or other short range wireless communication methodology can be determined by the wireless transceiver 138 and the processor 134.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A kiosk, comprising:
   a housing, comprising a hollow interior and a central opening defined horizontally through the housing;
   a display screen provided to the housing and facing horizontally outward from the housing;
   a thermal imaging sensor provided to the housing and located such that the thermal imaging sensor can read a body temperature of a person standing adjacent to the kiosk;
   a user-facing camera provided to the housing and located such that the user-facing camera can capture an image of the person standing adjacent to the kiosk;
   a dispenser nozzle provided to the housing and located such that a metered quantity of hand sanitizer can be dispensed on a hand of the person standing adjacent to the kiosk when the hand is placed in the central opening, and
   a processor, memory and wireless transceiver disposed within the housing, the processor coupled to the memory, the wireless transceiver, the display screen, the user-facing camera and the thermal imaging sensor, wherein the processor is configured to execute software code stored in the memory to perform an evaluation of the person standing adjacent to the kiosk,
   wherein the evaluation of the person standing adjacent to the kiosk comprises issuing a health query to the person standing adjacent to the kiosk and utilizing voice recognition to recognize a response to the health query by the person standing adjacent to the kiosk.

2. The kiosk of claim 1, further comprising an optical sensor provided to the housing and located such that the optical sensor can monitor the hand of the person standing adjacent to the kiosk when the hand is placed in the central opening.

3. The kiosk of claim 1, further comprising a speaker provided to the housing and a microphone provided to the housing.

4. The kiosk of claim 1, further comprising an access card reader provided to the housing.

5. The kiosk of claim 1, further comprising an access door defined in the housing and located such that at least some internal components of the kiosk can be accessed when the door is opened.

6. The kiosk of claim 1, further comprising a sanitizer reservoir and a pump disposed inside of the housing, wherein the pump is fluidically coupled to the sanitizer reservoir and to the dispenser nozzle.

7. The kiosk of claim 1, further comprising a light provided to the central opening and located such that the light illuminates the hand of the person standing adjacent to the kiosk when the hand is placed in the central opening.

8. The kiosk of claim 7, wherein the light provided to the central opening is configured to change colors to signify that the person standing adjacent to the kiosk has successfully sanitized their hand.

9. The kiosk of claim 1, wherein the evaluation of the person standing adjacent to the kiosk comprises reading an identification of the person standing adjacent to the kiosk.

10. The kiosk of claim 9, wherein the reading of the identification of the person standing adjacent to the kiosk comprises facial recognition.

11. The kiosk of claim 1, wherein the evaluation of the person standing adjacent to the kiosk comprises reading the body temperature of the person standing adjacent to the kiosk with the thermal imaging sensor.

12. The kiosk of claim 1, wherein the evaluation of the person standing adjacent to the kiosk comprises issuing a health query to the person standing adjacent to the kiosk and utilizing gesture recognition to recognize a response to the health query by the person standing adjacent to the kiosk.

13. The kiosk of claim 1, wherein the kiosk is networked with a central control computer, and the processor is configured to transmit a result data from the evaluation of the person standing adjacent to the kiosk.

14. The kiosk of claim 1, wherein the processor of the kiosk is configured to issue the person standing adjacent to the kiosk a quick-response (QR) code upon completion of the evaluation.

15. The kiosk of claim 1, wherein the processor of the kiosk is configured to unlock a door upon completion of the evaluation.

16. A method of evaluating a person attempting to gain entry to a premises by an automated kiosk, the method comprising:

the automated kiosk recognizing the presence of a person standing adjacent to the kiosk;

the kiosk reading a body temperature of the person standing adjacent to the kiosk;

the kiosk determining an identity of the person standing adjacent to the kiosk;

the kiosk dispensing a quantity of hand sanitizer upon a hand of the person standing adjacent to the kiosk;

the kiosk monitoring the hand of the person standing adjacent to the kiosk to ensure that proper sanitization of the hand is performed;

the kiosk issuing a series of health queries to the person standing adjacent to the kiosk; and the kiosk recognizing a response to the health queries by the person standing adjacent to the kiosk.

17. The method of claim 16, further comprising the kiosk unlocking a point of access of the premises to permit entry to the premises.

18. The method of claim 16, further comprising the kiosk maintaining a tally of persons allowed entry to the premises.

19. A kiosk, comprising:

a housing, comprising a hollow interior and a central opening defined horizontally through the housing;

a display screen provided to the housing and facing horizontally outward from the housing;

a thermal imaging sensor provided to the housing and located such that the thermal imaging sensor can read a body temperature of a person standing adjacent to the kiosk;

a user-facing camera provided to the housing and located such that the user-facing camera can capture an image of the person standing adjacent to the kiosk;

a dispenser nozzle provided to the housing and located such that a metered quantity of hand sanitizer can be dispensed on a hand of the person standing adjacent to the kiosk when the hand is placed in the central opening; and a light provided to the central opening and located such that the light illuminates the hand of the person standing adjacent to the kiosk when the hand is placed in the central opening, wherein the light provided to the central opening is configured to change colors to signify that the person standing adjacent to the kiosk has successfully sanitized their hand.

20. The kiosk of claim 19, further comprising a processor, memory and wireless transceiver disposed within the housing, the processor coupled to the memory, the wireless transceiver, the display screen, the user-facing camera and the thermal imaging sensor, wherein the processor is configured to execute software code stored in the memory to perform an evaluation of the person standing adjacent to the kiosk.

* * * * *